United States Patent [19]

Wepplo

[11] Patent Number: 4,474,962

[45] Date of Patent: Oct. 2, 1984

[54] PROCESS FOR THE PREPARATION OF PYRIDYL AND QUINOLYL IMIDAZOLINONES

[75] Inventor: Peter J. Wepplo, Princeton, N.J.

[73] Assignee: American Cyanamid Company, Stamford, Conn.

[21] Appl. No.: 489,399

[22] Filed: May 5, 1983

Related U.S. Application Data

[63] Continuation-in-part of Ser. No. 381,817, May 25, 1982, abandoned.

[51] Int. Cl.³ .......................................... C07D 401/04

[52] U.S. Cl. .................................... 546/167; 546/15; 546/278

[58] Field of Search ......................... 546/167, 278, 15

[56] References Cited

PUBLICATIONS

Brown, Synthesis, vol. 7, (1975), pp. 358–375.

Primary Examiner—Alan L. Rotman
Assistant Examiner—Bernard Dentz
Attorney, Agent, or Firm—H. G. Jackson

[57] ABSTRACT

There is provided a novel process for the preparation of pyridyl and quinolyl imidazolinones.

11 Claims, No Drawings

PROCESS FOR THE PREPARATION OF PYRIDYL AND QUINOLYL IMIDAZOLINONES

This application is a continuation-in-part of Ser. No. 381,817 filed May 25, 1982 now abandoned.

SUMMARY OF THE DISCLOSURE

In accordance with the process of the invention, formula (I) pyridyl and quinolyl imidazolinones can be prepared by a procedure involving heating, from about 1 to 20 equivalents and preferably at least 1.5 equivalents and most preferably 1.5 to 1.0 equivalents, of a 5-substituted formula (II) 2-picoline with at least 1 equivalent of an appropriate formula (III) aminocarboxamide in the presence of at least 3 equivalents and preferably 3 to 5 equivalents of sulfur. In this reaction, at least a 3 to 1 ratio of sulfur to aminocarboxamide and at least 1 and preferably 1.5 equivalents of the picoline is essential for good product yields. The reaction may optionally be conducted in a solvent which has a boiling point within the reaction temperature range. With regard to the picoline, it should be recognized that the compound, while being a reactant, may also be used as a solvent for the reaction and used in large excess. The reaction mixture is boiled, generally at a temperature between 100° and 250° C., and the vapors therefrom either distilled off or passed through a column packed with molecular sieves to remove any water formed during reaction. The dried condensed reaction mixture is then returned to the reaction vessel, and heating of the mixture is continued for several hours. Thereafter, the mixture is cooled, dissolved in an organic solvent such as ethyl acetate, diethyl ether or the like and filtered. The filtrate is extracted with an aqueous mineral acid such as sulfuric acid or hydrochloric acid, and the aqueous phase treated with aqueous base to liberate the formula (I) imidazolinone. If the product precipitates as a solid, it is recovered by filtration; if as an oil, it is extracted into a solvent such as dichloromethane, ether, and the like, and the product purified by conventional methods. The reaction may be graphically illustrated as follows:

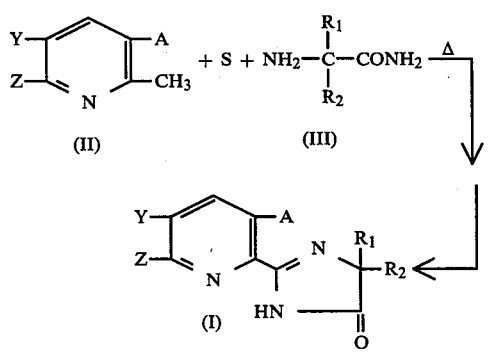

wherein Z is hydrogen; Y is hydrogen, chlorine, fluorine, $C_1-C_6$ alkyl, $C_1-C_6$ alkoxy, phenyl or substituted phenyl; A is hydrogen, primary or secondary $C_1-C_6$ alkyl or $COOR_3$ where $R_3$ is $C_1-C_{12}$ alkyl and $R_1$ and $R_2$ are $C_1-C_4$ alkyl or when taken together they may represent $C_3-C_6$ cycloalkyl optionally substituted with methyl and when $R_1$ and $R_2$ are not the same, the optical isomers thereof; and when taken together, Y and Z may form a ring in which YZ is

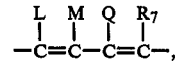

where L, M, Q and $R_7$ each represent members selected from the group consisting of hydrogen, chlorine, fluorine, methyl, methoxy or phenyl; A, $R_1 R_2$ and $R_3$ are as described above and when $R_1$ and $R_2$ are not the same the optical isomers thereof. This process is described in the co-pending application for U.S. Letters Patent of Marinus Los, Ser. No. 382,041, filed May 25, 1982 and incorporated herein by reference thereto. The process is thus highly effective for preparing variously substituted formula (I) imidazolinones from 2-picolines and substituted quinaldines.

Preparation of the 5-alkoxy-2-picoline employed in the above reaction for the preparation of 2-(5-alkoxy-2-pyridiyl)-5,5-di(lower)alkyl-2-imidazolin-4-one compounds is achieved by reacting 5-hydroxy-2-methylpyridine with an equivalent amount of a $C_1-C_4$ alkyl iodide in the presence of sodium hydride and a solvent such as dry dimethylformamide at a temperature of from 0° to 30° C. under a blanket of inert gas such as nitrogen.

As indicated above, the process of the invention is unique since it provides an unexpectedly effective method for the conversion, in a single step, of a substituted 2-picoline or substituted quinaldine to the herbicidally active pyridyl and quinolyl imidazolinones represented by formula (I) and for intermediates for herbicidally active acids of formula (I) in which A=COOH.

The closest art process of which I am aware is commonly referred to as the Willgerodt reaction.

It is apparent from reviews of the Willgerodt reaction [e.g. Synthesis, 358 (1975)], that the Kindler modification utilizes dry amines, ammonia, primary and secondary amines, to give thioamides. This reaction of 2-picoline, sulfur and aniline is described and can be illustrated as follows:

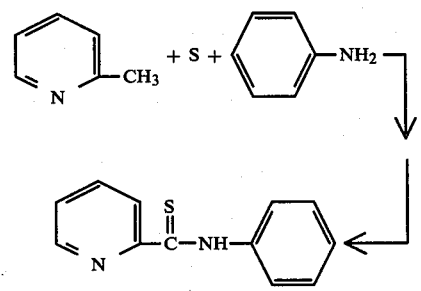

Clearly, the above process of Willgerodt does not suggest or render obvious the process of my invention which involves the discovery that when the amine in the above process, is replaced by an α-aminocarboxamide of the formula:

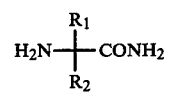

wherein $R_1$ and $R_2$ are $C_1-C_4$ alkyl groups, the reaction produces directly, in one step, the heterocyclic formula (I) imidazolinones, which are herbicides and/or intermediates for the preparation of herbicides.

As will be evident from the data provided below, the above formula (I) pyridyl and quinolyl imidazolinones are highly effective herbicidal agents or intermediates for the preparation of highly effective herbicides, useful for the control of a wide variety of annual and perennial monocotyledonous and dicotyledonous plants. They are also effective as aquatic herbicides. The compounds may be used for the control of undesirable plant species by applying to the foliage of the plants or to soil or water containing seeds or other propagating organs of the plants, a herbicidally effective amount of a formula (I) pyridyl or quinolyl imidazolinone. In practice the compounds are generally effective as herbicidal agents when applied at a rate sufficient to provide from about 0.016 to 10 kg/ha and preferably 0.016 to 4 kg/ha.

Among the compounds prepared by the process of this invention, which are effective as herbicides or are intermediates thereof are: 5-isopropyl-5-methyl-2-(2-pyridyl)-2-imidazolin-4-one; 5-isopropyl-5-methyl-2-(3-methyl-2-pyridyl)-2-imidazolin-4-one; ethyl 2-(5-isopropyl-5-methyl-4-oxo-2-imidazolin-2-yl)nicotinate; ethyl-(5-isopropyl-5-methyl-4-oxo-2-imidazolin-2-yl)-3-quinolinecarboxylate.

Highly effective herbicides can be prepared from the 2-(2-pyridyl)- and 2-(2-quinolyl)imidazolinones of formula (I) in which A=H by treatment of same with butyl lithium followed by carbon dioxide. Among the compounds prepared by this process which are effective herbicies are: 2-(5-isopropyl-5-methyl-4-oxo-2-imidazolin-2-yl)nicotinic acid; 2-(5-isopropyl-5-methyl-4-oxo-2-imidazolin-2-yl)-3-quinolinecarboxylic acid; 5-ethyl-2-(5-isopropyl-5-methyl-4-oxo-2-imidazolin-2-yl)nicotinic acid; 2-(5-isopropyl-5-methyl-4-oxo-2-imidazolin-2-yl)-5-phenylnicotinic acid; 2-(5-isopropyl-5-methyl-4-oxo-2-imidazolin-2-yl)-5-methoxynicotinic acid, 2-(5-isopropyl-5-methyl-4-oxo-2-imidazolin-2-yl)-5-isopropoxynicotinic acid and 5-ethoxy-2-(5-isopropyl-5-methyl-4-oxo-2-imidazolin-2-yl)nicotinic acid.

For application as pre-emergence, postemergence or aquatic herbicides, the formula (I) imidazolinones can be formulated as wettable powders, flowable concentrates, emulsifiable concentrates, granular formulations and the like.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxyalcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not to be deemed limited thereby. Unless otherwise noted, all parts are by weight.

EXAMPLE 1

Preparation of the intermediate 5-ethoxy-2-methylpyridine

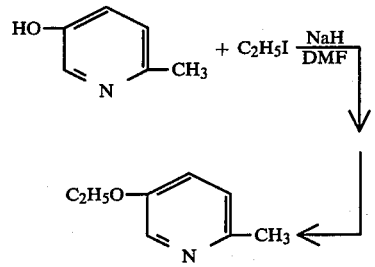

To a stirred suspension of 16.6 g sodium hydride in 500 ml dry dimethylformamide (DMF) under nitrogen at 0° C. is added 90 g 5-hydroxy-2-methylpyridine at such a rate that the temperature remains between 0°–5° C. When gas evolution ceases, 73.8 ml ethyl iodide in 100 ml DMF is added dropwise. After stirring at room temperature overnight, the mixture is diluted with water and extracted with ether. The ether extracts are washed with brine, dried and concentrated. This oil is distilled to give 62.5 g of 5-ethoxy-2-methylpyridine, bp 89°–91° C. at 12 mm.

Using the above procedure but substituting isopropyl iodide for ethyl iodide there is obtained 5-isopropoxy-2-methylpyridine, bp 95°–100° C./0.15 mm.

EXAMPLE 2

Preparation of 2-(5-ethoxy-2-pyridyl)-5-isopropyl-5-methyl-2-imidazolin-4-one

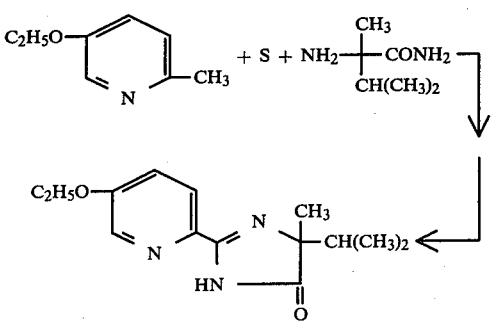

A mixture of 60.5 g 5-ethoxy-2-picoline, 38.3 g 2-amino-2,3-dimethylbutyramide and 28.25 g sulfur is heated with stirring under nitrogen. At 160° C. a liquid boils which is condensed and returned to the flask through a tube packed with molecular sieves to absorb water formed in the reaction. The temperature of the mixture slowly rises to 185° C. and is held there for 2.5 hours. The mixture is cooled, dissolved in 500 ml ethyl acetate and filtered. The filtrate is extracted with 6×100 ml portions of 2N hydrochloric acid. The aqueous phases are combined, the pH adjusted to 7 with 50% aqueous sodium hydroxide. A solid precipitate forms which is collected. The mother liquor is extracted with methylene chloride, the extracts dried and concentrated. The residue is triturated with etherhexane to give a crystalline solid which is removed and thoroughly washed with hexane and dried. Both solids are combined to give 23.7 g product. Two recrystallizations of a sample from methylene chloride-hexane gives analytically pure 2-(5-ethoxy-2-pyridyl)-5-isopropyl-5-methyl-2-imidazolin-4-one, mp 143°–145° C.

Using essentially the same procedure described above but substituting the appropriate substituted α-picoline or quinaldine for 5-ethoxy-2-picoline. The following imidazolinones are prepared:

| Substituent | mp °C. |
|---|---|
| none | 90–93 |
| 5-$C_2H_5$ | 67–71 |
| 5-$OCH_3$ | 166–167.5 |
| 5-$C_6H_5$ | 150–151.5 |
| 3-$CH_3$ | 93–96 |
| 3-$COOC_2H_5$ | 72–75 |
| 5-$OCH(CH_3)_2$ | 126–128 |
| 3-$C_2H_5$ | 73–75 |
| 5-$C_2H_5$ | 64–66, $[\alpha]_D^{20} = +5.3°$ (C = 0.05 g/ml THF) |

| Substituent | mp °C. |
|---|---|
| none | 143–144 |
| 3-$COOC_2H_5$ | 146–147.5 |
| none | 113.5–115.5, $[\alpha] = +18.75°$ (C = .027 g/ml EtOH) |

EXAMPLE 3

Preparation of 5-ethoxy-2-(5-isopropyl-5-methyl-4-oxo-2-imidazolin-2-yl)nicotinic acid

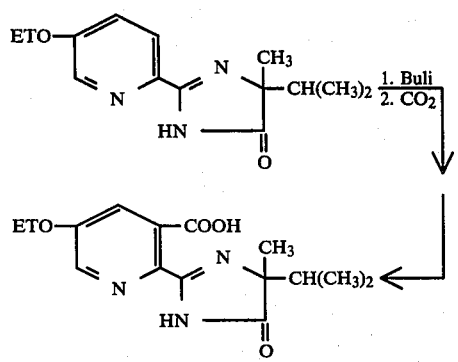

To a stirred solution containing 13.5 g ethoxypyridine derivative in 250 ml dry THF at −70° C. under nitrogen is added dropwise 65 ml of 1.8 m solution of butyl lithium in hexane without allowing the temperature to rise above −65° C. After a further 2 hours at −70° C., 15 ml butyl lithium solution is added dropwise and stirring continued for 0.5 hours. Solid carbon dioxide in excess is then added to the reaction mixture and the mixture allowed to attain room temperature. The solvent is removed, the residue taken up in 250 ml water, the pH adjusted to 8 with 6N $H_2SO_4$ and extracted with $CH_2Cl_2$. The organic phase is discarded. The pH of the aqueous phase is adjusted to 3. The precipitate (3.8 g) is collected and dried. The filtrate is extracted with $CH_2Cl_2$. TLC of the extract showed the presence of some starting material. The organic phase is extracted with 4×100 ml saturated sodium bicarbonate solution. These are combined, acidified with concentrated $H_2SO_4$ to pH 3 to give a solid (4.5 g) identical with the solid collected above. A sample recrystallized from acetonitrile has mp 140°–144° C. (decomposes) and is analytically pure 5-ethoxy-2-(5-isopropyl-5-methyl-4-oxo-2-imidazolin-2-yl)nicotinic acid.

Using essentially the same procedure described above but substituting the appropriately substituted 5-isopropyl-5-methyl-2-(2-pyridyl)- or -2-(2-quinolyl)-2-imidazolin-4-one for 2-(5-ethoxy-2-pyridyl)-5-isopropyl-5-methyl-2-imidazolin-4-one, the following nicotinic or quinoline-3-carboxylic acids are prepared.

| Y | Z | mp °C. |
|---|---|---|
| $C_2H_5$ | H | 172–175.0 |
| $OCH_3$ | H | 166–167.5 |
| $C_6H_5$ | H | 150–151.5 |
| $OCH(CH_3)_2$ | H | 83–85 |
| H | H | 170–172.5 |
| $C_2H_5$ | H | 121–123, $[\alpha]_D^{20} = +13.4°$ (C = 0.0908 g/ml THF) |

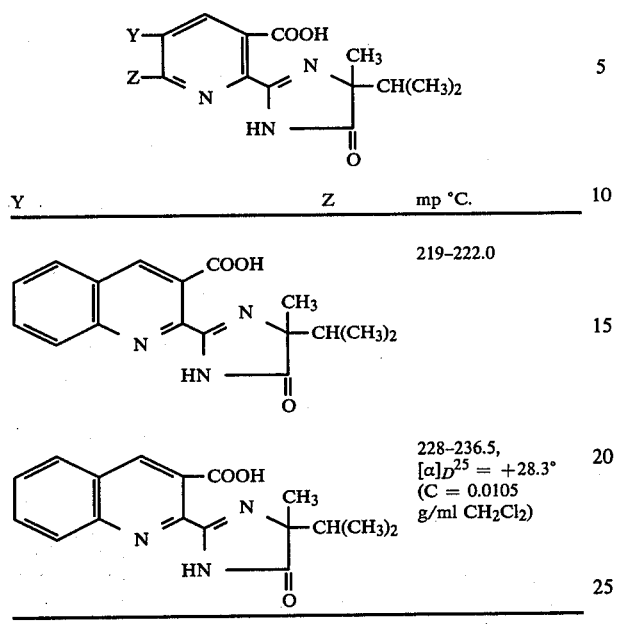

| Y | Z | mp °C. |
|---|---|---|
| (fused benzene) | | 219–222.0 |
| (fused benzene) | | 228–236.5, $[\alpha]_D^{25} = +28.3°$ (C = 0.0105 g/ml $CH_2Cl_2$) |

EXAMPLE 4

Preparation of 2-(5-isopropoxy-2-pyridyl)-5-isopropyl-5-methyl-2-imidazolin-4-one

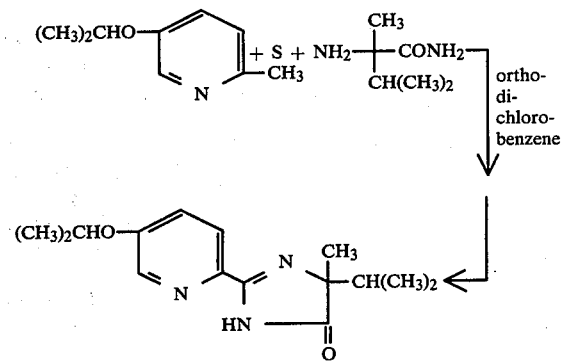

ortho-di-chloro-benzene

A mixture containing 1.97 kg of 5-isopropoxy-2-picoline, 2.09 kg of 2-amino-2,3-dimethylbutyramide and 1.78 kg of sulfur in 7.5 liters of ortho-dichlorobenzene is heated to 180° C. while stirring under nitrogen. After stirring at 180° C. for 10 hours, the mixture is cooled to room temperature and clarified by filtration. The filtrate is extracted with 19 liters of 4.5% aqueous hydrochloric acid and the aqueous layer separated off.

Methylene chloride (10 liters) is added to the aqueous extract and the pH of the mixture adjusted to pH 6.5 with 50% aqueous sodium hydroxide. The organic phase is separated and the aqueous layer extracted with additional methylene chloride (2 liters). The organic extracts are combined, dried over anhydrous $MgSO_4$, filtered and concentrated on a rotary evaporator. The residue is slurried with heptanes for one hour and the resulting solid filtered off and dried to yield 904 g of 2-(5-isopropoxy-2-pyridyl)-5-isopropyl-5-methyl-2-imidazolin-4-one.

EXAMPLE 5

Preparation of 2-(5-ethyl-2-pyridiyl)-5-isopropyl-5-methyl-2-imidazolin-4-one

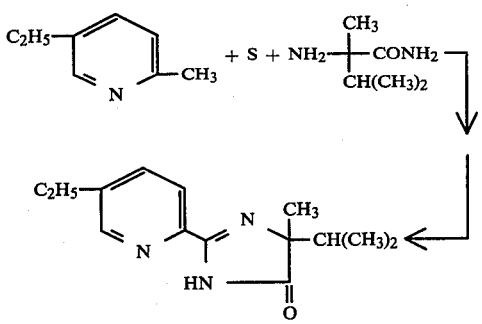

A mixture of 183.8 g 5-ethyl-2-picoline, 40.0 g 2-amino-2,3-dimethylbutyramide and 29.6 g sulfur is heated to 180°–190° C. with stirring under nitrogen. The temperature of the mixture slowly rises to 180°–90° C. while low boiling components are collected in a Dean Stark Trap, and held there for 3 hours. The mixture is cooled and the excess picoline removed by distillation under reduced pressure., dissolved in 200 mL ethyl acetate and filtered. The filtrate is extracted with 6×100 mL portions of 2N hydrochloric acid. The aqueous phases are combined, the pH adjusted to 8 with 50% aqueous sodium hydroxide. The solution is extracted with ethyl acetate 5×150 mL, the extracts combined, treated with activated charcoal, filtered and concentrated. This affords 56.7 g (75% yield) of 2-(5-ethyl-2-pyridyl-5-isopropyl-5-methyl-2-imidazolin-4-one, as a red gum which is 94.9% pure.

EXAMPLE 6

Preparation of 2-(5-isopropyl-5-methyl-4-oxo-imidazolin-2-yl)nicotinic acid

A solution of potassium tertiary-butoxide (2.8 g, 0.025 mol) in dimethylformamide (DMF 10 mL) is added dropwise to a stirred solution of 2-(3-methyl-2-pyridyl)-5-isopropyl-5-methyl-2-imidazolin-4-one (1.2 g 0.005 mol) in dry DMF while bubbling oxygen through the reaction mixture. Upon completion of the addition the mixture is stirred at 40°–50° C. for three hours, then it is cooled, clarified by filtration, and diluted with water (50 mL). The pH of the aqueous solution is adjusted to pH 2 and the product extracted into ethyl acetate.

The organic solution is dried over $MgSO_4$, filtered and the solvent removed under reduced pressure to yield 0.76 g (57% yield) of 2-(5-isopropyl-5-methyl-4-oxo-2-imidazolin-2-yl)nicotinic acid, mp 166°–167° C.

EXAMPLE 7

Post-emergence herbicidal evaluation of test compounds

The post-emergence herbicidal activity of the compounds of the invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN ®
20, a polyoxyethylene sorbitan monolaurate surfactant
of Atlas Chemical Industries, in sufficient quantity to
provide the equivalent of about 0.025 kg of 8 kg per
hectare of active compound when applied to the plants
through a spray nozzle operating at 40 psi for a predetermined time. After spraying, the plants are placed on
greenhouse benches and are cared for in the usual manner, commensurate with conventional greenhouse practices. From 4 to 5 weeks after treatment, the seedling
plants, are examined and rated according to the rating
system provided below. The data obtained are recorded
in Table I below.

| Rating System | % Difference in Growth from the Check* |
| --- | --- |
| 0 No effect | 0 |
| 1 Possible effect | 1–10 |
| 2 Slight effect | 11–25 |
| 3 Moderate effect | 26–40 |
| 5 Definite injury | 41–60 |
| 6 Herbicidal effect | 61–75 |
| 7 Good Herbicidal effect | 76–90 |
| 8 Approaching complete kill | 91–99 |
| 9 Complete kill | 100 |
| 4 Abnormal growth, that is, a definite physiological malformation but with an over-all effect less than a 5 on the rating scale. | |

In most cases the data are for a single test, but in several
instances, they are average values obtained from more
than one test.

| Plant Species Used | |
| --- | --- |
| Barnyardgrass | (Echinochloa crusgalli) |
| Green foxtail | (Setaria viridis) |
| Purple Nutsedge | (Cyperus rotundus L.) |
| Wild Oats | (Avena Fatua) |
| Quackgrass | (Agropyron repens) |
| Field Bindweed | (Convolvulus arvensis L.) |
| Morningglory | (Ipomoea purpurea) |
| Ragweed | (Ambrosia artemisiifolia) |
| Velvetleaf | (Abutilon Theophrasti) |
| Barley | (Hordeum vulgare) |
| Corn | (Zea mays) |
| Rice | (Oryza Sativa) |
| Soybean | (Glycine max) |
| Sunflower | (Helianthus annus) |
| Wheat | (Triticum aestivum) |

TABLE I
POST-EMERGENCE TESTS - RATES IN KG/HA

| Compound | RATE | BARN-YARD GR | GREEN FOX | P NUT SEDGE | WILD OATS | QUACK GRASS | FLD BIND-WD | MRNGLRY SP | RAG-WEED | VELVET-LEAF | BARLEY LA (S) | CORN FIELD | RICE, NATO | SOYBEAN WI | SUNFLR XXX | WHEAT ER (S) |
|---|---|---|---|---|---|---|---|---|---|---|---|---|---|---|---|---|
| Ethyl 2-(5-isopropyl-5-methyl-4-oxo-2-imidazolin-2-yl) nicotinate | 8.000 | 8.0 | 9.0 | 9.0 | 9.0 | 9.0 | 9.0 | 8.0 | 9.0 | 9.0 | 9.0 | 9.0 | 8.0 | 9.0 | 9.0 | 9.0 |
|  | 1.000 | 7.0 | 9.0 | 8.0 | 9.0 | 9.0 | 9.0 | 9.0 | 9.0 | 9.0 | 9.0 | 8.0 | 8.0 | 9.0 | 9.0 | 9.0 |
|  | .500 | 3.0 | 9.0 | 7.0 | 9.0 | 9.0 | 9.0 | 9.0 | 8.0 | 9.0 | 9.0 | 8.0 | 6.0 | 8.0 | 9.0 | 8.0 |
|  | .250 | 0.0 | 8.0 | 7.0 | 8.0 | 8.0 | 9.0 | 9.0 | 8.0 | 9.0 |  |  |  |  |  |  |
| 5-Isopropyl-5-methyl-2-(2-pyridyl)-2-imidazolin-4-one | 8.000 |  |  | 2.0 |  |  |  | 7.0 | 7.0 | 6.0 |  |  |  |  |  |  |
| 5-Isopropyl-5-methyl-2-(3-methyl-2-pyridyl)-2-imidazolin-4-one | 8.000 | 0.0 | 7.0 | 9.0 | 9.0 | 9.0 | 5.0 | 8.0 | 7.0 | 8.0 | 0.0 | 0.0 | 0.0 | | 0.0 | 0.0 |
|  | 1.000 | 0.0 | 0.0 | 0.0 | 0.0 | 6.0 | 4.0 | 2.0 | 0.0 | 4.0 |  |  |  |  |  |  |
| 2-(5-Isopropyl-5-methyl-4-oxo-2-imidazolin-2-yl)-5-phenylnicotinic acid | 2.000 | 9.0 | 9.0 | 4.0 | 9.0 | 4.0 | 9.0 | 6.0 | 7.0 | 9.0 |  | 9.0 | 7.0 |  | 9.0 | 9.0 |
|  | 1.000 | 8.5 | 8.0 | 1.5 | 9.0 | 1.5 | 7.0 | 7.0 | 4.5 | 9.0 |  | 9.0 | 7.5 |  | 8.0 | 6.0 |
|  | .500 | 8.5 | 7.0 | 1.0 | 7.0 | 0.0 | 6.5 | 6.5 | 4.0 | 9.0 |  | 9.0 | 6.5 |  | 7.5 | 4.5 |
|  | .250 | 7.5 | 7.0 | 0.0 | 8.0 | 1.0 | 4.0 | 5.0 | 1.0 | 5.5 |  | 9.0 | 6.5 |  | 8.0 | 1.5 |
| Ethyl 2-(5-isopropyl-5-methyl-4-oxo-2-imidazolin-2-yl)-3-quinoline carboxylate | 4.000 | 9.0 | 8.0 | 7.0 | 9.0 | 6.0 | 6.0 | 7.0 | 7.0 | 7.0 |  | 9.0 | 4.0 |  | 7.0 | 6.0 |
|  | 1.000 | 7.0 | 5.0 | 3.0 | 8.0 | 4.0 | 4.0 | 3.0 | 7.0 | 3.0 |  | 9.0 | 3.0 |  | 7.0 | 7.0 |
|  | .500 | 2.0 | 5.0 | 3.0 | 8.0 |  | 4.0 | 3.0 | 0.0 | 3.0 |  | 4.0 | 3.0 |  | 6.0 | 3.0 |
|  | .250 |  | 5.0 | 1.0 | 8.0 | 1.0 | 1.0 | 1.0 | 0.0 | 1.0 |  | 3.0 | 3.0 |  | 6.0 | 3.0 |
| 2-(5-Isopropyl-5-methyl-4-oxo-2-imidazolin-2-yl)-3-quinoline carboxylic acid | 8.000 | 9.0 | 9.0 | 9.0 | 9.0 | 9.0 | 9.0 | 9.0 | 9.0 | 9.0 |  | 9.0 | 9.0 | 0.5 | 9.0 | 9.0 |
|  | 4.000 | 9.0 | 9.0 | 9.0 | 9.0 | 9.0 | 9.0 | 8.5 | 8.5 | 9.0 |  | 9.0 | 9.0 | 0.0 | 9.0 | 9.0 |
|  | 2.000 | 9.0 | 9.0 | 8.5 | 9.0 | 9.0 | 9.0 | 8.3 | 8.8 | 9.0 |  | 9.0 | 8.7 | 0.1 | 9.0 | 8.9 |
|  | 1.000 | 9.0 | 9.0 | 8.3 | 9.0 | 8.9 | 8.7 | 8.3 | 8.0 | 8.6 |  |  |  | 3.0 |  |  |
|  | .800 | 9.0 | 8.8 | 6.8 | 9.0 | 8.8 | 8.8 | 6.8 | 8.4 | 8.3 | 9.0 | 9.0 | 8.3 | 4.0 | 9.0 | 8.8 |
|  | .500 | 8.9 | 8.9 | 7.6 |  | 8.6 | 8.3 | 7.7 | 7.5 | 7.7 |  |  |  | 2.7 |  |  |
|  | .400 | 9.0 | 8.5 | 6.5 | 9.0 | 7.8 |  | 6.0 | 9.0 | 7.8 | — | | | 3.0 | | |
| 5-Ethyl 2-(5-isopropyl-5-methyl-4-oxo-2-imidazolin-2-yl)nicotinic acid | 1.000 | 9.0 | 9.0 | 9.0 | 9.0 | 9.0 | 9.0 | 9.0 | 9.0 | 9.0 | 4.0 | 9.0 | 9.0 | 4.0 | 9.0 | 9.0 |
|  | .500 | 9.0 | 9.0 | 9.0 | 9.0 | 9.0 | 9.0 | 9.0 | 9.0 | 9.0 | 4.0 | 9.0 | 9.0 | 5.0 | 9.0 | 9.0 |
|  | .250 | 9.0 | 9.0 | 9.0 | 9.0 | 9.0 | 9.0 | 9.0 | 9.0 | 9.0 |  |  |  | 5.0 |  |  |
| 2-(5-Isopropyl-5-methyl-4-oxo-2-imidazolin-2-yl)nicotonic acid | 10.000 | 9.0 | 9.0 | 9.0 | 9.0 | 9.0 |  | 7.0 | 9.0 | 9.0 | 9.0 | 9.0 | 9.0 | 9.0 | 9.0 | 9.0 |
|  | 2.000 | 9.0 | 9.0 | 9.0 | 9.0 | 9.0 | 8.8 | 8.0 | 8.0 | 9.0 | 9.0 | 9.0 | 9.0 | 9.0 | 9.0 | 9.0 |
|  | 1.000 | 9.0 | 9.0 | 9.0 | 9.0 | 9.0 | 9.0 | 8.8 | 8.8 | 9.0 | 9.0 | 9.0 | 8.8 | 9.0 | 9.0 | 9.0 |
|  | .500 | 9.0 | 9.0 | 8.7 | 9.0 | 9.0 | 9.0 | 8.8 | 8.6 | 8.9 |  |  | 8.8 |  |  |  |
|  | .250 | 8.9 | 9.0 | 8.8 | 9.0 | 9.0 | 9.0 | 8.9 | 8.6 | 8.9 |  |  |  |  |  |  |
| 2-(5-Isopropyl-5-methyl-4-oxo-2-imidazolin-2-yl)-5-isopropoxynicotinic acid | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
|  | .500 | 9.0 | 9.0 | 9.0 | 9.0 | 9.0 | 9.0 | 9.0 | 8.5 | 9.0 | 9.0 | 9.0 | 9.0 | 9.0 | 9.0 | 9.0 |
|  | .250 | 9.0 | 9.0 | 9.0 | 9.0 | 9.0 | 9.0 | 9.0 | 9.0 | 9.0 | 9.0 | 9.0 | 8.0 | 9.0 | 9.0 | 9.0 |
| 5-Ethoxy-2-(5-isopropyl-5-methyl-4-oxo-2-imidazolin-2-yl)nicotinic acid | | | | | | | | | | | | | | | | |

EXAMPLE 8

Pre-emergence herbicidal evaluation of test compounds

The pre-emergence herbicidal activity of the compounds of the invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.025 to 8 kg per hectare of test compound per cup. The treated cups are then placed on greenhouse benches, watered and cared for in accordance with conventional greenhouse procedures. From 4 to 5 weeks after treatment, the tests are terminated and each cup is examined and rated according to the rating system set forth above. The herbicidal proficiency of the active ingredients of the present invention is evident from the test results which are recorded in Table II below. Where more than one test is involved for a given compound, the data are averaged.

TABLE II

PRE-EMERGENCE TESTS - RATES IN KG/HA

| Compound | RATE | BARN-YARD GR | GREEN FOX | P NUT SEDGE | WILD OATS | QUACK GRASS | FLD BIND-WD | MRNGLRY SP | RAG-WEED | VELVET-LEAF | S BARLEY LA | CORN FIELD | RICE, NATO | SOYBEAN WI | SUNFLR XXX | S WHEAT ER |
|---|---|---|---|---|---|---|---|---|---|---|---|---|---|---|---|---|
| Ethyl 2-(5-iso-propyl-5-methyl-4-oxo-2-imidazolin-2-yl)nicotinate | 8.000 | 9.0 | 9.0 | 9.0 | 8.0 | | 9.0 | 8.0 | 9.0 | 8.0 | 9.0 | 9.0 | 9.0 | 9.0 | 9.0 | 9.0 |
| | .500 | 9.0 | 9.0 | 9.0 | 9.0 | | 9.0 | 9.0 | 9.0 | 9.0 | 9.0 | 9.0 | 9.0 | 9.0 | 9.0 | 9.0 |
| | .250 | 8.0 | 9.0 | 9.0 | 9.0 | | | 9.0 | | 9.0 | | | | | | |
| 5-Isopropyl-5-methyl-2-(2-pyridyl)-2-imidazolin-4-one | 8.000 | 6.0 | 8.0 | 3.0 | 8.0 | | | 2.0 | 2.0 | 8.0 | | | | | | |
| 5-Isopropyl-5-methyl-2-(3-methyl-2-pyridyl)-2-imidazolin-4-one | 8.000 | 7.0 | 9.0 | 9.0 | 9.0 | 9.0 | 9.0 | 8.0 | 8.0 | 8.0 | 9.0 | 1.0 | 2.0 | | 3.0 | 3.0 |
| | .500 | 0.0 | 4.0 | 0.0 | 4.0 | 2.0 | 9.0 | 3.0 | 6.0 | 4.0 | 3.0 | 1.0 | 1.0 | | 2.0 | 1.0 |
| | .250 | 0.0 | 1.0 | 0.0 | 3.0 | 1.0 | 9.0 | | 0.0 | 3.0 | | | | | | |
| 2-(5-Isopropyl-5-methyl-4-oxo-2-imidazolin-2-yl)-5-phenylnicotinic acid | 4.000 | 3.0 | 8.0 | 1.0 | 4.0 | 9.0 | 9.0 | 2.0 | 1.0 | 3.0 | | 9.0 | 9.0 | | 5.0 | 7.0 |
| | 1.000 | 1.0 | 8.0 | 0.0 | 2.0 | 9.0 | 6.0 | 1.0 | 0.0 | 3.0 | | 3.0 | 9.0 | | 2.0 | 4.0 |
| | .500 | 0.0 | 2.0 | 0.0 | 1.0 | 0.0 | 2.0 | 0.0 | 0.0 | 0.0 | | 3.0 | 6.0 | | 2.0 | 2.0 |
| | .250 | 0.0 | 0.0 | 0.0 | 1.0 | 0.0 | 0.0 | 0.0 | 0.0 | 0.0 | | 1.0 | 5.0 | | 2.0 | 2.0 |
| Ethyl 2-(5-isopropyl-5-methyl-4-oxo-2-imidazolin-2-yl)-3-quinolinecarboxylate | 4.000 | 9.0 | 9.0 | 9.0 | 9.0 | 9.0 | 9.0 | 8.0 | 9.0 | 9.0 | | 9.0 | 9.0 | | 9.0 | 9.0 |
| | 1.000 | 9.0 | 9.0 | 7.0 | 9.0 | 9.0 | 9.0 | 6.0 | 7.0 | 8.0 | | 9.0 | 7.0 | | 8.0 | 8.0 |
| | .500 | 8.0 | 4.0 | 5.0 | 2.0 | 0.0 | 8.0 | 3.0 | 4.0 | 7.0 | | 4.0 | 3.0 | | 4.0 | 4.0 |
| | .250 | 3.0 | 2.0 | 3.0 | | 3.0 | 0.0 | 0.0 | 0.0 | 6.0 | | 3.0 | 1.0 | | 3.0 | 2.0 |
| 2-(5-Isopropyl-5-methyl-4-oxo-2-imidazolin-2-yl)-5-methoxynicotinic acid | .500 | 9.0 | | 9.0 | 9.0 | 9.0 | 9.0 | 9.0 | 9.0 | 9.0 | | 9.0 | 9.0 | 9.0 | 9.0 | 9.0 |
| | .250 | 9.0 | | 9.0 | 9.0 | 9.0 | 9.0 | 9.0 | 9.0 | 9.0 | | 9.0 | 9.0 | 9.0 | 9.0 | 9.0 |
| 2-(5-Isopropyl-5-methyl-4-oxo-2-imidazolin-2-yl)nicotinic acid | 8.000 | 9.0 | 9.0 | 9.0 | 9.0 | 9.0 | 9.0 | 8.0 | 9.0 | 8.0 | 9.0 | 9.0 | 9.0 | 9.0 | 9.0 | 9.0 |
| | 4.000 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | 1.000 | 9.0 | 9.0 | 9.0 | 9.0 | 9.0 | 9.0 | 9.0 | 9.0 | 8.8 | | 9.0 | 9.0 | 6.5 | 9.0 | 9.0 |
| | .250 | 8.3 | 8.8 | 9.0 | 8.6 | 9.0 | 9.0 | 8.0 | 7.9 | 7.9 | | 8.8 | 9.0 | 3.6 | 8.6 | 8.6 |
| 5-Ethyl-2-(5-isopropyl-5-methyl-2-yl)nicotinic acid | .500 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 | 9.0 | 9.0 | 9.0 | 8.0 | 9.0 | 9.0 | 9.0 |
| 2-(5-Isopropyl-5-methyl-4-oxo-2-imidazolin-2-yl)nicotinic acid | 10.000 | 8.0 | 9.0 | 9.0 | 8.0 | 9.0 | 9.0 | 8.0 | 8.0 | 8.0 | 9.0 | 9.0 | 9.0 | 8.0 | 9.0 | 9.0 |
| | 2.000 | 9.0 | 9.0 | 9.0 | 9.0 | 9.0 | 9.0 | 8.0 | 9.0 | 9.0 | 9.0 | 9.0 | 9.0 | 8.5 | 9.0 | 9.0 |
| | 1.000 | 9.0 | 9.0 | 9.0 | 9.0 | 9.0 | | 8.0 | 9.0 | 9.0 | 9.0 | 9.0 | 9.0 | 8.7 | 9.0 | 9.0 |
| | .500 | 9.0 | 9.0 | 9.0 | 9.0 | 9.0 | 9.0 | 8.7 | 8.8 | 8.8 | 9.0 | 9.0 | 9.0 | 8.7 | 9.0 | 9.0 |
| | .250 | 9.0 | 9.0 | 9.0 | 9.0 | 9.0 | 9.0 | 8.8 | 8.8 | 8.8 | 9.0 | 9.0 | 9.0 | 8.7 | 9.0 | 9.0 |
| 2-(5-Isopropyl-5-methyl-4-oxo-2-imidazolin-2-yl)-5-isopropoxynicotinic acid | 1.000 | 9.0 | 9.0 | 9.0 | 9.0 | 9.0 | 9.0 | 9.0 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 8.5 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 7.0 | 9.0 | 9.0 | 9.0 | 8.0 | 9.0 | 9.0 | 9.0 |
| 2-(5-Isopropyl-5-methyl-4-oxo-2-imidazolin-2-yl)-5-methoxynicotinic acid | | | | | | | | | | | | | | | | |

TABLE II-continued
PRE-EMERGENCE TESTS - RATES IN KG/HA

| Compound | RATE | BARN-YARD GR | GREEN FOX | P NUT SEDGE | WILD OATS | QUACK GRASS | FLD BIND-WD | MRNGLRY SP | RAG-WEED | VELVET-LEAF | BARLEY LA S | CORN FIELD | RICE, NATO | SOYBEAN WI | SUNFLR XXX | WHEAT ER S |
|---|---|---|---|---|---|---|---|---|---|---|---|---|---|---|---|---|
| 5-Ethoxy-2-(5-isopropyl-5-methyl-4-oxo-2-imidazolin-2-yl)nicotinic acid | | | | | | | | | | | | | | | | |

I claim:

1. A method for the preparation of a compound of the formula:

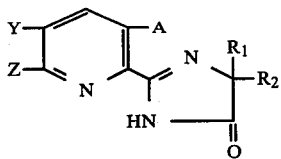

wherein Z is hydrogen; Y is hydrogen, chlorine, fluorine, $C_1$-$C_6$ alkyl, $C_1$-$C_6$ alkoxy, phenyl or substituted phenyl; A is hydrogen, $C_1$-$C_6$ primary or secondary alkyl or $COOR_3$ where $R_3$ is $C_1$-$C_{12}$ alkyl and $R_1$ and $R_2$ are $C_1$-$C_4$ alkyl or when taken together they may represent $C_3$-$C_6$ cycloalkyl optionally substituted with methyl and when $R_1$ and $R_2$ are not the same, the optical isomers thereof; and when taken together, Y and Z may form a ring in which YZ is

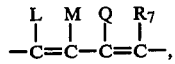

where L, M, Q and $R_7$ each represent members selected from the group consisting of hydrogen, chlorine, fluorine, methyl, methoxy or phenyl; A, $R_1$, $R_2$ and $R_3$ are as described above and when $R_1$ and $R_2$ are not the same the optical isomers thereof, comprising reacting from 1 to 20 equivalents of a compound of the formula:

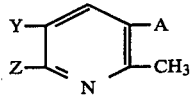

wherein A, Y and Z are as described above; with at least 3 equivalents of sulfur and about 1 equivalent of an aminocarboxamide of the formula:

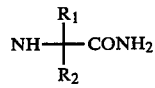

wherein $R_1$ and $R_2$ are as described above; at an elevated temperature.

2. A method according to claim 1 wherein 1.5 to 10 equivalents of α-picoline is reacted with 3 to 5 equivalents of sulfur and 1 equivalent of aminocarboxamide at a temperature between 100° and 200° C.

3. A method according to claim 1 wherein A and Z are hydrogen; Y is $C_1$-$C_6$ alkoxy; $R_1$ is methyl and $R_2$ is isopropyl.

4. A method according to claim 1 wherein Y is $C_1$-$C_6$ alkyl; A and Z are hydrogen; $R_1$ is methyl and $R_2$ is isopropyl.

5. A method according to claim 1 wherein Y and Z are taken together and represent

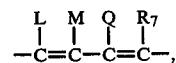

where L, M, Q and $R_7$ each represent members selected from the group consisting of hydrogen, chlorine, fluorine, methyl, methoxy or phenyl; A is as described in claim 1; $R_1$ is methyl and $R_2$ is isopropyl.

6. A method according to claim 1 wherein Y is phenyl; Z is hydrogen; A is as described in claim 1; $R_1$ is methyl and $R_2$ is isopropyl.

7. A method according to claim 1 wherein Y is ethyl, A and Z are hydrogen, R is methyl and $R_2$ is isopropyl.

8. A method according to claim 1 wherein Y and Z are hydrogen, A is $CH_3$, $R_1$ is $CH_3$, $R_2$ is $CH(CH_3)_2$.

9. A method according to claim 1 wherein Y and Z are hydrogen, A is $COOR_3$, $R_1$ is $CH_3$, $R_2$ is $CH(CH_3)_2$ and $R_3$ is as described in claim 1.

10. A method according to claim 1 wherein Y and Z are —CH=CH—CH=CH—, A is $COOR_3$, $R_1$ is $CH_3$, $R_2$ is $CH(CH_3)_2$ and $R_3$ is as described in claim 1.

11. A method according to claim 1 wherein 1,5 equivalents of α-picoline or quinaldine is heated to from 100° to 250° C. with 3 equivalents of sulfur and 1 equivalent of the α-aminocarboxamide to obtain the desired pyridyl or quinolyl imidazolinone.

* * * * *